United States Patent [19]

Breitschuh

[11] Patent Number: 5,763,638
[45] Date of Patent: Jun. 9, 1998

[54] PREPARATION OF AROMATIC NITRILES

[75] Inventor: Richard Breitschuh, Berlin, Germany

[73] Assignee: Ciba Specialty Chemicals Corporation, Tarrytown, N.Y.

[21] Appl. No.: 795,718

[22] Filed: Feb. 4, 1997

[30] Foreign Application Priority Data

Feb. 15, 1996 [CH] Switzerland ............... 39096

[51] Int. Cl.⁶ .................. C07C 253/00; C07D 213/84
[52] U.S. Cl. .................. 558/314; 544/124; 546/145; 546/176; 546/193; 546/230; 546/286; 546/287; 546/288; 546/289
[58] Field of Search ............... 558/315, 314; 546/286

[56] References Cited

U.S. PATENT DOCUMENTS 5,349,103  9/1994  Gülec ............... 558/314
5,618,965  4/1997  Kudschus ............... 558/315

FOREIGN PATENT DOCUMENTS 0080700  4/1986  European Pat. Off. .
0550762  7/1993  European Pat. Off. .
0609179  8/1994  European Pat. Off. .
0731086  9/1996  European Pat. Off. .
117872   2/1976  Germany .

OTHER PUBLICATIONS

Derwent Abstr. 76–31977X/18 (1976).

Chemical Abstract—85:93176e (1976).

Synthesis, 112–113, 1979.

Chemical Abstract 114:206700 (1991); Huaxue Shiji (1990), 12(5), 314.292.

Chemical Abstract—114;101296d; Nanjing Univ. 26(2), 263–6 (1990).

J. of Chem. Soc. Part IX, p. 43 (1933).

Synthesis, p. 190 & 191 (1982).

*Primary Examiner*—Michael G. Ambrose
*Attorney, Agent, or Firm*—Kevin T. Mansfield

[57] ABSTRACT

A process for the preparation of nitriles of formula

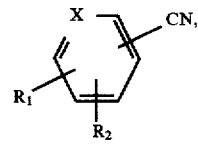

(I)

wherein X is CH or N, and $R_1$ and $R_2$ are each independently of the other hydrogen, chloro, bromo, $C_1$–$C_6$alkyl, $C_1$–$C_6$alkoxy, $C_1$–$C_6$alkylamino, CN, phenyl, phenoxy, dimethylamino, piperidyl, morpholinyl or pyrrolidyl, or $R_1$ and $R_2$ together form a fused benzene ring, by reacting an aldehyde of formula

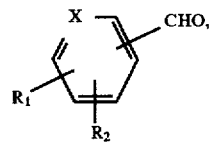

(II)

with hydroxylaminosulfate in the presence of a tertiary amine base of formula

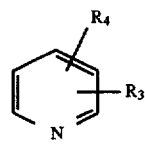

(III)

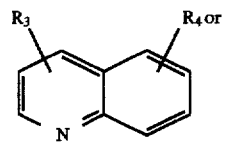

(IV)

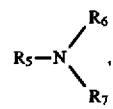

(V)

wherein $R_3$ and $R_4$ are each independently of the other hydrogen, methyl or ethyl, $R_5$ is branched $C_3$–$C_5$alkyl or phenyl, and $R_6$ and $R_7$ are methyl or ethyl, in the temperature range from 100° to 160° C., while distilling the released water of reaction off concomittantly at a pressure in the range of 0.02 to 1.5 bar, with subsequent removal of the ammonium salts, and isolating the nitrile so obtained by customary methods.

10 Claims, No Drawings

PREPARATION OF AROMATIC NITRILES

The present application relates to the preparation of aromatic nitriles by reacting corresponding aldehydes with hydroxylaminosulfate in a water-immiscible organic solvent in the presence of a tertiary amine base.

The reaction of aldehydes with hydroxylamine salts and subsequent dehydration of the oxime obtained to the nitrile has been known for a long time. Different methods have been proposed for dehydration, e.g. in C.A. 85, 93176e (1976) by heating in dimethylformamide, in Synthesis 1979, 2, 112–113 and in Huaxue Shiji 1990, 12(5), 314, 292, by heating in formic acid, in Journal of Nanjing Univ. 1990, 26(2), 263–266, by heating in formic acid or glacial acetic acid, and in J. Chem. Soc. 1933, IX, 43 by heating in acetic anhydride. Today, the use of dimethylformamide on a large industrial scale is to be avoided wherever possible owing to toxicological and environmental considerations. The use of formic acid gives very good results but cannot be recommended because of its strong caustic activity, its toxicity and elaborate regeneration.

According to a method proposed in U.S. Pat. No. 5,349,103, these disadvantages can be avoided by replacing the formic acid with propionic acid, which still gives a satisfactory yield. The propionic acid distilled off with the forming water can be regenerated, but only in a separate step.

Synthesis 1982, 190 describes a method using a hydroxylammonium chloride/pyridine/toluene system. The sublimating pyridinium chloride which forms in this process renders the isolation of the desired end product considerably more difficult. According to EP-B 80700, dehydration of the oxime to the nitrile is achieved by distilling off the water azeotropically using a water-immiscible solvent forming an azeotropic mixture. The yields so obtained are not always satisfactory.

Surprisingly, it has now been found that reacting aromatic aldehydes with hydroxylaminosulfate, where appropriate in a water-immiscible solvent forming an azeotropic mixture, in the presence of a tertiary amine base results in very good nitrile yields, which nitrile can be purified of the pyridinium hydrogen sulfate by phase separation without any problems and the solvent which may be present can be recycled direct by distillation during the reaction process, which is of great importance with respect to environmental policy.

Accordingly, this invention relates to a process for the preparation of nitriles of formula

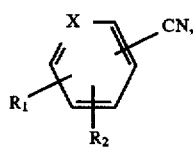    (I)

wherein X is CH or N, and $R_1$ and $R_2$ are each independently of the other hydrogen, chloro, bromo, $C_1$–$C_6$alkyl, $C_1$–$C_6$alkoxy, $C_1$–$C_6$alkylamino, CN, phenyl, phenoxy, dimethylamino, piperidyl, morpholinyl or pyrrolidyl, or $R_1$ and $R_2$ together form a fused benzene ring, by reacting an aldehyde of formula

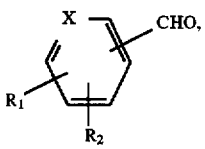    (II)

wherein X, $R_1$ and $R_2$ have the meaning given above, with hydroxylaminosulfate and with subsequent dehydration, which comprises carrying out the reaction in the presence of a tertiary amine base of formula

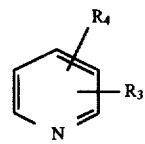    (III)

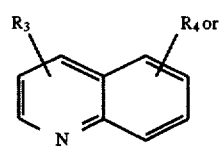    (IV)

or

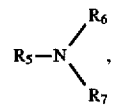    (V)

wherein $R_3$ and $R_4$ are each independently of the other hydrogen, methyl or ethyl, $R_5$ is branched $C_3$–$C_5$alkyl or phenyl, and $R_6$ and $R_7$ are methyl or ethyl, in the temperature range from 100° to 160° C., preferably from 120° to 150° C., while distilling the released water of reaction off concomittantly at a pressure in the range of 0.02 to 1.5 bar, preferably in the range of 0.1 bar to atmospheric pressure, with subsequent removal of the ammonium salts, typically by phase separation, with or without prior addition of water, and isolating the nitrile so obtained by customary methods.

The reaction is carried out according to the following reaction scheme:

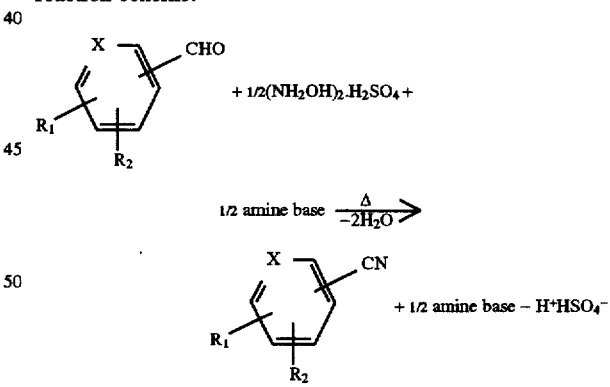

The reaction is conveniently carried-out in the presence of a water-immiscible solvent forming an azeotropic mixture which preferably boils in the temperature range from 100° to 170° C., typically heptane, octane, methylcyclohexane, cumene, benzene and, preferably, toluene.

$R_1$ and $R_2$ defined as $C_1$–$C_6$alkyl are typically methyl, ethyl, n-propyl, isopropyl, n-butyl, sec-butyl, tert-butyl, n-pentyl, tert-amyl or n-hexyl, and defined as $C_1$–$C_6$alkoxy they are typically methoxy, ethoxy, isopropoxy, n-butoxy, tert-butoxy, tert-amyloxy or hexyloxy.

$R_1$ and $R_2$ defined as $C_1$–$C_6$alkylamino are typically methylamino, ethylamino, isopropyl-amino, tert-butylamino, n-pentylamino, hexylamino.

$R_5$ defined as branched $C_3$–$C_6$alkyl is typically isopropyl, tert-butyl or tert-amyl.

Illustrative examples of tertiary amine bases of formula III are pyridine, 2-picoline, 2,6-lutidine, 5-ethyl-2-methylpyridine, those of formula IV are typically quinaldine, and those of formula V are typically N,N-dimethylaniline, N,N-diethylaniline or dimethylisopropylamine. Preferred amine bases are those of formula III as well as dimethylaniline and diethylaniline. Dimethylaniline and, especially, pyridine are particularly preferred.

The process of this invention is of particular interest for the preparation of nitrites of formula I, wherein X is CH, $R_2$ is hydrogen, and $R_1$ is hydrogen, $C_1$–$C_4$alkyl or phenyl and is in para position to the cyano group.

The aldehydes of formula II are known compounds. Any of them that may still be novel can be prepared in general accordance with known methods.

The amine base of the amine base-$H^+HSO_4^-$ salt resulting from the reaction can be recycled and used again by the addition of a base, e.g. sodium hydroxide solution.

The hydroxylaminosulfate is used in approximately stoichiometric amounts, but preferably in stoichiometric amount or in slight excess, i.e. from 0.50 to 0.58 mol per 1 mol of aldehyde.

The amine base is conveniently used in an amount from 1.0 to 1.5 mol per 1 mol of hydroxylaminosulfate.

The nitrites obtainable by the novel process are valuable intermediates, inter alia for the preparation of the diketopyrrolopyrrole pigments which have proven their worth for some years and which are now termed, also in the literature, e.g. in Colour Index, DPP pigments.

The following Examples illustrate the invention in more detail.

EXAMPLE 1

Over 1.5–2 hours, a total of 502.3 g (3.0 mol) of hydroxylaminosulfate are added in 4 increments to 735.7 g (6 mol) of 4-methylbenzaldehyde, 81 g of water, 286.2 g (3.6 mol) of pyridine and 720 g of toluene at 35°–60° C., such that subsequent additions are only carried out once the hydroxylaminosulfate added earlier is completely dissolved. A further 720 g of toluene are then added and the reaction mixture is refluxed with a water separator. At about 95° C. the reaction mass starts to boil and, after distillation of about 200 ml of water, an internal temperature of 118° C. is reached. The reaction mixture is heated with the water separator until 240–250 ml of water are distilled off. After distilling off half of the toluene, water is again distilled off at an internal temperature of by then 126°–129° C. until water separation markedly diminishes (entire period of water separation and toluene distillation: about 8 hours). The mixture is cooled to 70°–80° C., the lower phase (pyridinium salts) is removed, the upper phase is washed once with 250–300 ml of water, and the residual water and the toluene are distilled off at in the end 120° C./50 mbar. 641 g (89% of theory) of pale yellow fused 4-methylbenzonitrile (m.p.: 119° C. at 40 mbar) remain, having a purity of above 97% (HPLC)*. The nitrile can be further purified by subsequent distillation.

* HPCL=High Performance Liquid Chromatography

EXAMPLE 2

20.0 g (0.2 mol) of 98% sulfuric acid are added dropwise to 490.6 g (4 mol) of 4-methylbenzaldehyde and 19.8 g (0.25 mol) of pyridine, and the mixture so obtained is then heated. At 130°–140° C. and 180 mbar, a total of 197.8 g (2.5 mol) of pyridine and 334.9 g (2.0 mol) of hydroxylaminosulfate are added in small portions over a period of about 5 hours, the water of reaction being distilled off while the entrained aldehyde/nitrile mixture is returned. After addition of the last portion, the mixture is heated for another hour at 130°–140° C./100 mbar and is then cooled to 70°–80° C. and the lower phase (fused pyridinium salts) is removed. The remaining crude product is washed with an additional 100 ml of water, the residual water is distilled off at 116° C./40 mbar, and then 368.0 g of colourless 4-methyl-benzonitrile (78% of theory) are distilled off at in the end 115° C./28 mbar, which solidify at 28° C. The melt of pyridinium sulfate and pyridinium hydrogen sulfate removed earlier is diluted with 400 g of water and adjusted to pH 8.5 with 548 g (4.11 mol) of 30% sodium hydroxide. Upon removal of the lower phase, which consists of sodium sulfate and water, 288 g of pyridine having a water content of 25–30% remain which can be used again for the next batch without any further purification.

EXAMPLE 3

167.5 g (1 mol) of hydroxylaminosulfate are added in 4 portions to 331 g (2 mol) of 4-tert-butylbenzaldehyde, 146.8 g (1.2 mol) of 5-ethyl-2-methylpyridine, 45 g of water and 250 g of toluene at 40°–60° C. When all the hydroxylaminosulfate is dissolved, 550 g of toluene are added and the mixture is heated to reflux with a water separator. After separation of 99 ml of water, half of the toluene is distilled off, the boiling point rising from 119° C. to 126° C., and water is distilled off until less than 2 ml per hour separate. The lower phase is then removed at 50° C., the organic phase is washed in two portions with the water of reaction, the residual water is distilled off azeotropically and the toluene is distilled off at in the end 136° C./50 mbar. The remaining residue is 295 g (88% of theory) of 4-tert-butylbenzonitrile in the form of a golden brown oil having a content of 95% (HPLC)* and which can be further purified by distillation (m.p.=120° C./10 mbar).

* HPCL=High Performance Liquid Chromatography

EXAMPLE 4

335 g (2 mol) of hydroxylaminosulfate are added in 2 portions to 662 g (4 mol) of 4-tert-butylbenzaldehyde, 292.3 g (2.4 mol) of N,N-dimethylaniline, 90 g of water and 800 g of xylene at 60°–90° C. and the reaction mixture is then refluxed with a water separator. Upon separation of about 210 ml of water, the mixture is cooled to 70° C. and the water distilled off earlier is added. The lower aqueous phase is then removed, the organic phase is washed with an additional 100 ml of water and the xylene is distilled off at in the end 150° C./50 mbar. 625.4 g (86% of theory) of 88% (HPLC)* 4-tert-butylbenzonitrile remain. For further purification it is possible to either remove the amide which crystallises out during cooling by filtration or to purify the nitrile by distillation.

* HPCL=High Performance Liquid Chromatography

EXAMPLE 5

372 g (2 mol) of 4-phenylbenzaldehyde are charged to 800 g of xylene, 45 g of water and 111.8 g (1.2 mol) of 2-picoline at 50° C. and then 167.5 g (1 mol) of hydroxylaminosulfate are added in 4 increments at 50°–65° C. The mixture is refluxed with a water separator until water separation markedly diminishes after 6–7 hours. The mixture is then cooled to about 100° C., the 114 ml of water which were distilled off earlier are added and the lower phase (water+picoline salts) is removed at about 90° C. The organic phase is washed with an additional 100 ml of water at 90° C., the resulting solution is clarified by filtration and the xylene is distilled off at in the end 150° C./70 mbar. The remaining residue is 318.4 g (81% of theory) of a pale brown melt of 4-phenylbenzonitrile having an analytical content of 91% (HPLC)* and which solidifies at 80°–85° C.

* HPCL=High Performance Liquid Chromatography

What is claimed is:

1. A process for the preparation of a nitrile of formula

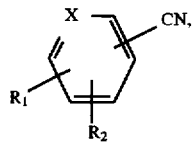

wherein X is CH or N, and $R_1$ and $R_2$ are each independently of the other hydrogen, chloro, bromo, $C_1$–$C_6$alkyl, $C_1$–$C_6$alkoxy, $C_1$–$C_6$alkylamino, CN, phenyl, phenoxy, dimethylamino, piperidyl, morpholinyl or pyrrolidyl, or $R_1$ and $R_2$ together form a fused benzene ring, by reacting an aldehyde of formula

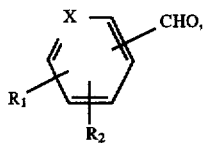

wherein X, $R_1$ and $R_2$ have the meaning given above, with hydroxylaminosulfate and with subsequent dehydration, which comprises carrying out the reaction in the presence of a tertiary amine base of formula

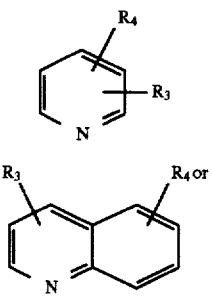

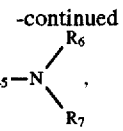

wherein $R_3$ and $R_4$ are each independently of the other hydrogen, methyl or ethyl, $R_5$ is branched $C_3$–$C_5$alkyl or phenyl, and $R_6$ and $R_7$ are methyl or ethyl, in the temperature range from 100° to 160° C., while distilling the released water of reaction off concomittantly at a pressure in the range of 0.02 to 1.5 bar, with subsequent removal of the ammonium salts by phase separation with or without prior addition of water, and isolating the nitrile so obtained from the organic phase.

2. The process according to claim 1, which comprises carrying out the reaction in the presence of a water-immiscible organic solvent forming an azeotropic mixture.

3. The process according to claim 2, wherein the solvent is chlorobenzene or toluene.

4. The process according to claim 1, which comprises using a tertiary amine base selected from the group consisting of pyridine, 2-picoline, 2,6-lutidine, 5-ethyl-2-methylpyridine, quinaldine, N,N-dimethylaniline, N,N-diethylaniline and dimethylisopropylamine.

5. The process according to claim 4, which comprises using pyridine or dimethylaniline.

6. The process according to claim 1 for the preparation of a nitrile of formula I, wherein X is CH, $R_2$ is hydrogen, and $R_1$ is hydrogen, $C_1$–$C_4$alkyl or phenyl and is in para position to the cyano group.

7. The process according to claim 1, wherein the hydroxylaminosulfate is used in an amount of 0.5 to 0.58 mol per 1 mol of aldehyde.

8. The process according to claim 7, wherein the amine base is used in an amount of 1.0 to 1.5 mol per 1 mol of hydroxylaminosulfate.

9. The process according to claim 1 wherein the temperature range is from 120° to 150° C.

10. The process according to claim 1 wherein the released water of reaction is distilled off concomittantly at a pressure in the range of 0.1 bar to atmospheric pressure.

* * * * *